(12) United States Patent
El-Gamal

(10) Patent No.: US 11,795,179 B2
(45) Date of Patent: Oct. 24, 2023

(54) DISCOVERY OF IMIDAZOTHIAZOLE- AND IMIDAZOOXAZOLE-BASED SELECTIVE HER4 KINASE INHIBITORS AS POTENTIAL ANTICANCER AGENTS

(71) Applicant: University of Sharjah, Sharjah (AE)

(72) Inventor: Mohammed El-Gamal, Sharjah (AE)

(73) Assignee: UNIVERSITY OF SHARJAH, Sharjah (AE)

( * ) Notice: Subject to any disclaimer, the term of this patent is extended or adjusted under 35 U.S.C. 154(b) by 0 days.

(21) Appl. No.: 17/137,706

(22) Filed: Dec. 30, 2020

(65) Prior Publication Data
US 2022/0204528 A1    Jun. 30, 2022

(51) Int. Cl.
*C07D 513/04*    (2006.01)

(52) U.S. Cl.
CPC .................. *C07D 513/04* (2013.01)

(58) Field of Classification Search
CPC ........................................ C07D 513/04
USPC ........................................ 514/274
See application file for complete search history.

(56) References Cited

FOREIGN PATENT DOCUMENTS

WO    WO-2018008920 A1 *    1/2018    ........... A61K 31/424

OTHER PUBLICATIONS

A.B. Nair, "A simple practice guide for dose conversion between animals and human" Article, 2016, 27-31, vol. 7, No. 2, Journal of Basic and Clinical Pharmacy.

* cited by examiner

*Primary Examiner* — Kahsay Habte
(74) *Attorney, Agent, or Firm* — Hayes Soloway PC

(57) ABSTRACT

Novel first-in-class imidazothiazole- and imidazooxazole-based potent and selective HER4 kinase inhibitors for therapeutic formulations and methods for treating cancer.

9 Claims, 13 Drawing Sheets

X = S, O, NH, N-(C1-6 alkyl), N-(3-7 membered cycloalkyl);

Y = 0, O, NH, S (*para* or *meta* or *ortho*);

Z = CH, N;

$R^1$ = H, $SO_2CH_3$, $SO_2NH_2$, $SO_2NHalkyl(C_1-C_6)$, $NH_2$, N-alkyl, NH-aralkyl;

$R^2$ = H, C1-6 alkyl or isoalkyl, C3-8 cycloalkyl, arylmethyl, arylethyl, arylpropyl, haloarylmethyl, haloarylethyl, heteroarylmethyl, heteroarylethyl, heteroarylpropyl, heteroarylalkenyl, heteroarylalkynyl, alkenyl, and alkynyl.

R = H, Me, SO₂NH₂, Me₂NCH₂CH₂, *i*-PrNCH₂CH₂, 1-pyrrolidinyl-CH₂CH₂, 1-piperidinyl-CH₂CH₂, 4-morpholino-CH₂-CH₂, benzyl, *p*-F-benzyl, phenethyl, *p*-F-phenethyl (II)　　　　　　　　　　　　(III)

| Cell line | Cancer type |  | | Sorafenib (IC$_{50}$, µM) |
|---|---|---|---|---|
| | | % inhibition at 10 µM | IC$_{50}$ (µM) | |
| MOLT-4 | Leukemia | 73.53% | 1.02 | 3.16 |
| NCI-H522 | Non-small cell lung cancer | 94.09% | 4.91 | 5.01 |
| HCC-2998 | Colon cancer | 67.64% | 1.78 | 3.16 |
| U251 | CNS cancer | 10.94% | 6.08 | 2.00 |
| SK-MEL-5 | Melanoma | 99.86% | 0.507 | 2.51 |
| OVCAR-4 | Ovarian cancer | 26.22% | 3.78 | 3.16 |
| UO-31 | Renal cancer | 96.30% | 1.55 | 2.51 |
| DU-145 | Prostate cancer | 159.56% | 1.67 | 3.16 |
| MDA-MB-468 | Breast cancer | 165.07% | 1.04 | 2.00 |
| WI-38 | Normal cells | 56.43% | 8.54 | NT |

*Bold figures indicate stronger potency than sorafenib.*

| Cell line | Cancer type |  | | Sorafenib (IC$_{50}$, µM) |
|---|---|---|---|---|
| | | % inhibition at 10 µM | IC$_{50}$ (µM) | |
| HL-60(TB) | Leukemia | 56.33% | 3.36 | 1.58 |
| NCI-H322M | Non-small cell lung cancer | NT% | 1.82 | 2.51 |
| HCC-2998 | Colon cancer | 116.25% | 1.76 | 3.16 |
| SNB-75 | CNS cancer | 4.08% | 15.6 | 3.16 |
| SK-MEL-5 | Melanoma | 94.61% | 1.54 | 2.51 |
| OVCAR-4 | Ovarian cancer | 34.91% | 3.98 | 3.16 |
| UO-31 | Renal cancer | 124.08% | 1.68 | 2.51 |
| DU-145 | Prostate cancer | 153.83% | 1.89 | 3.16 |
| MDA-MB-468 | Breast cancer | 163.64% | 1.80 | 2.00 |
| WI-38 | Normal cells | 21.65% | 12.64 | NT |

*Bold figures indicate stronger potency than sorafenib.*

| Kinase | % inhibition | % inhibition |
| --- | --- | --- |
| B-RAF (wild-type) | 34.33% ± 5.62% | 9.62% ± 0.21% |
| c-SRC | -22.15% ± 0.91% | 2.46% ± 1.52% |
| EGFR (HER1) | 63.57% ± 1.26% | -5.54% ± 0.21% |
| ErbB2 (HER2) | 2.75% ± 0.26% | -2.99% ± 0.53% |
| ErbB4 (HER4) | 82.08% ± 0.37% | 53.42% ± 0.14% |
| FGFR1 | 3.33% ± 0.38% | -0.04% ± 0.04% |
| KDR (VEGFR2) | 24.78% ± 0.09% | 24.77% ± 0.07% |
| RAF1 | 23.00% ± 0.43% | 10.82% ± 2.78% |
| V600E-B-RAF | 62.15% ± 0.84% | 33.56% ± 2.19% |

*The results are expressed as means ± S.E.M.*

FIG. 8

| Kinase | % inhibition |
|---|---|
| AKT1 | -3.10% ± 0.26% |
| AKT2 | -29.36% ± 3.41% |
| BTK | 5.08% ± 0.38% |
| DAPK1 | -8.04% ± 1.22% |
| FAK | 10.05% ± 0.35% |
| FLT3 | 43.78% ± 1.47% |
| FLT3 (D835Y) | 8.06% ± 0.89% |
| FRK (PTK5) | 28.52% ± 2.35% |
| GSK3α | 13.00% ± 0.42% |
| GSK3β | -8.50% ± 0.45% |
| mTOR | 17.94% ± 1.95% |
| PI3K-C2α | -4.19% ± 0.12% |

*The results are expressed as means ± S.E.M.*

| Kinase | <br>IC$_{50}$ (nM) | Staurosporine<br>IC$_{50}$ (nM) |
|---|---|---|
| EGFR (HER1) | 9,920 | 39.8 |
| HER2 (P780_Y781insGSP) | >90,000 | 10.1 |
| HER2 (V777_G778insCG) | >90,000 | 64.9 |
| ErbB4 (HER4) | 26.9 | 138 |
| V600E-B-RAF | 13,200 | 8.77 |

| Compound | IC$_{50}$ (nM) |
|---|---|
|  | 26.9 |
|  | 719 |

| Compound | IC50 (nM) against hERG potassium ion channels |
|---|---|
| [chemical structure] | 12,410 |
| E-4031 (reference standard) | 24.2 |

FIG. 12

| Compound | IC50 (nM) | |
|---|---|---|
| | CYP 2D6 | CYP 3A4 |
|  | >90,000 | 17,800 |
| Ketoconazole (reference standard) | 8,310 | 2.38 |

DISCOVERY OF IMIDAZOTHIAZOLE- AND IMIDAZOOXAZOLE-BASED SELECTIVE HER4 KINASE INHIBITORS AS POTENTIAL ANTICANCER AGENTS

TECHNICAL FIELD

The present invention relates to novel selective HER4 kinase inhibitors as anticancer agents.

BACKGROUND OF THE INVENTION

Cancer has become one of the major health challenges that require continuous efforts to develop efficient drugs. It is the second leading cause of death globally after the cardiovascular disorders. The World Health Organization (WHO) expects increment of the number of newly discovered cancer cases to become 15 million cases worldwide every year.

Kinases are over-expressed in several diseases such as cancer. Kinase inhibition has been a hotspot approach for treatment of cancer. HER4 (ErbB4) kinase is a receptor tyrosine kinase that belongs to epidermal growth factor receptor subfamily. It is over-expressed as an oncogenic kinase in different types of cancer such as breast cancer, cervical cancer, melanoma, prostate cancer, and others. Inhibitors of this kinase can be potential anticancer agents for treatment of different types of cancer.

The kinase non-selectivity of a number of traditional kinase-inhibitory anticancer agents leads to narrow safety margins and a high risk of side effects. This has created a need for highly selective and potent inhibitors of HER4 (ErbB4) kinase with strong antiproliferative potency. Reported herein for the first time are selective HER4 (ErbB4) kinase inhibitors with novel scaffold reported for the first time against this kinase.

SUMMARY OF THE EMBODIMENTS

The invention is directed at novel derivatives of imidazothiazole- and imidazooxazole as selective inhibitors of HER4 (ErbB4) kinase.

Disclosed is the compound I for treating or preventing a cancer overexpressing HER4 kinase, comprising administering an effective amount of the compound to a patient having a cancer. In addition, the disclosed inhibitors can help molecular biologists investigate the biological roles of HER4 kinase in more details.

In certain embodiments, disclosed is herein the compound IA, comprising administering an effective amount of the compound to a patient having a cancer.

In certain embodiments, is further disclosed the compound IL, comprising administering an effective amount of the compound to a patient having a cancer.

In certain embodiments, is also disclosed the compound III, comprising administering an effective amount of the compound to a patient having a cancer.

Further disclosed is a method of treating a subject afflicted by a cancer associated with an altered expression of one or more kinases, comprising administering to the subject in need thereof a therapeutically effective amount of the compound I, a pharmaceutically acceptable salt thereof, and one or more pharmaceutical excipients.

In certain embodiments, is disclosed a method of treating a subject afflicted by a cancer associated with an altered expression of one or more kinases, comprising administering to the subject in need thereof a therapeutically effective amount of the compound II, a pharmaceutically acceptable salt thereof, and one or more pharmaceutical excipients.

In certain embodiments, is further disclosed a method of treating a subject afflicted by a cancer associated with an altered expression of one or more kinases, comprising administering to the subject in need thereof a therapeutically effective amount of the compound III, a pharmaceutically acceptable salt thereof, and one or more pharmaceutical excipients.

In certain embodiments, is further disclosed a kit for treating a subject with a cancer associated with an altered expression of one or more kinases, comprising the compounds of the present invention, or a pharmaceutically acceptable salt thereof, and one or more pharmaceutical excipients.

BRIEF DESCRIPTION OF THE FIGURES

The invention can be better understood with reference to the following figures and description.

FIG. 8 illustrates the percentage of inhibition of compounds II and III (10 μM) against a panel of 9 kinases.

FIG. 12 illustrates the potency (IC$_{50}$) of compound III against hERG potassium ion channel compared to E-4031 (reference standard).

DETAILED DESCRIPTION OF SPECIFIC EMBODIMENTS

Figure 1:
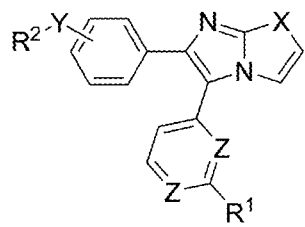
FIG. 1 illustrates the claimed compounds I.
Figure 2:
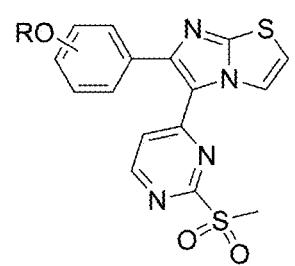
FIG. 2 illustrates compound I.A.
Figure 3:
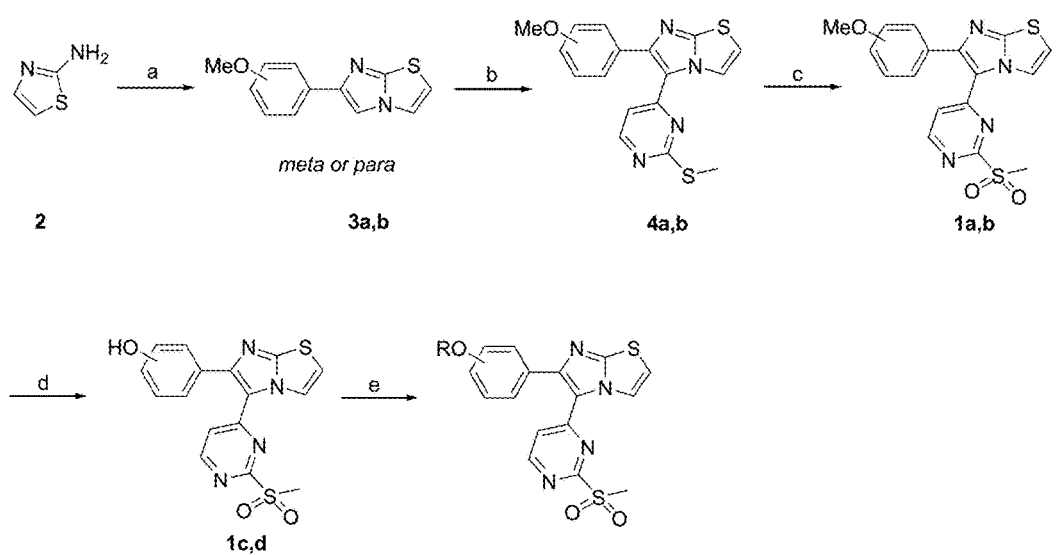
FIG. 3 illustrates the synthesis of compound I.A. Reagents and conditions: (a) α-bromo-3(4)-methoxyacetophenone, EtOH, reflux, 16 h; (b) 4-iodo-2-(methylthio)pyrimidine, Pd(OAc)$_2$, Cs$_2$CO$_3$, PPh$_3$, DMF, 80° C., 12 h; (c) oxone, MeOH, H$_2$O, rt, 16 h; (d) BBr$_3$, CH$_2$Cl$_2$, −78° C., 1 h; rt, overnight; (e) NaH, appropriate R—Br, DMF, rt, 1 h.
Figure 4:
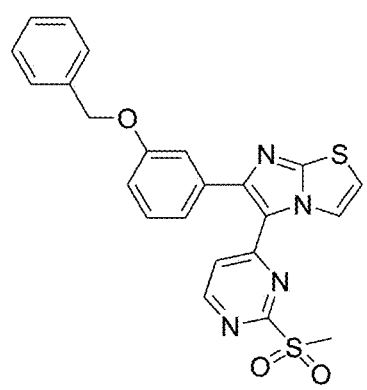
FIG. 4 illustrates compounds II and III.
Figure 4:
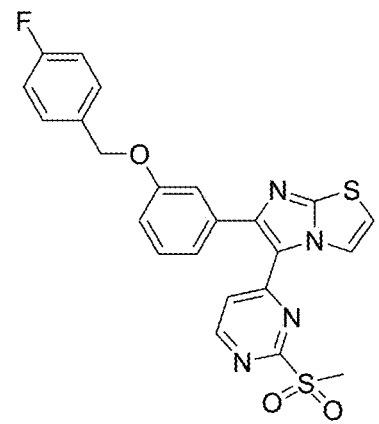
Figure 5:
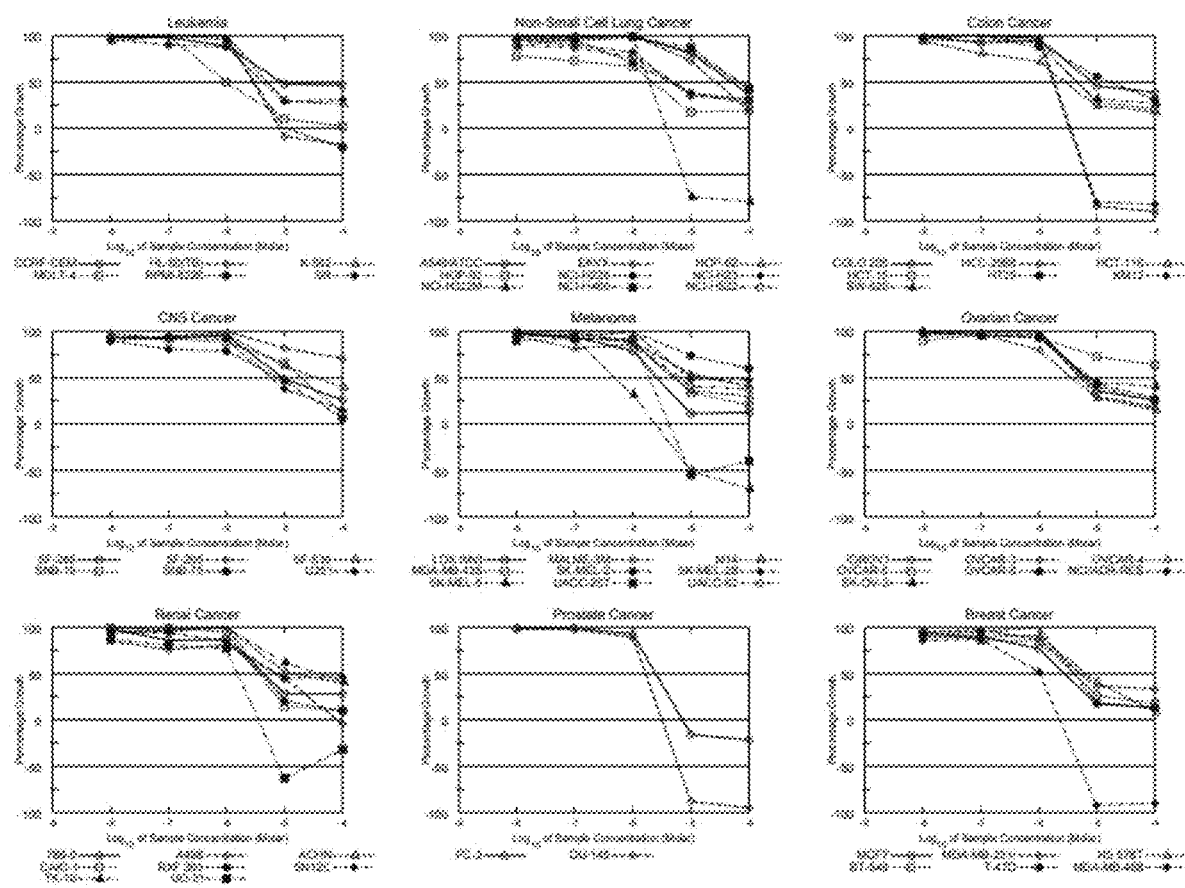
FIG. 5 illustrates dose-response curves of compound III against a panel of nine cell lines.
Figure 6:
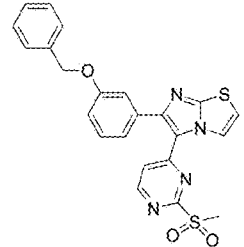
FIG. 6 illustrates IC$_{50}$ values and the percentage of inhibition of compound III at 10 μM against nine cell lines and normal cells and IC$_{50}$ values of Sorafenib as a reference standard.
Figure 7:
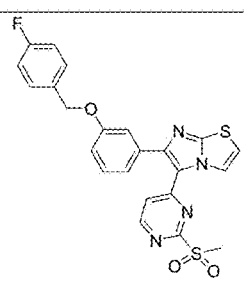
FIG. 7 illustrates IC$_{50}$ values and the percentage of inhibition of compound II (10 μM) against nine cell lines and normal cells and IC$_{50}$ values of Sorafenib as a reference standard.
Figure 9:
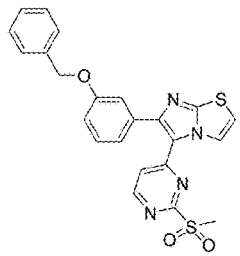
FIG. 9 illustrates the percentage of inhibition of compound III (10 μM) against another 12-kinase panel.
Figure 10:
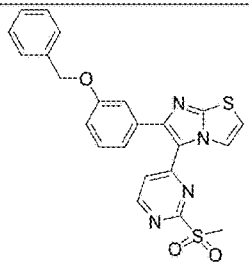
FIG. 10 illustrates the IC$_{50}$ values of compound III against the kinases that were inhibited by more than 50% at 10 μM concentration, compared to Staurosporine as a reference standard.
Figure 11:
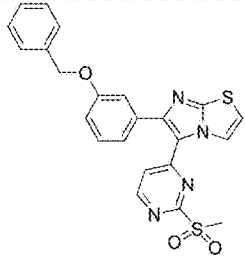
FIG. 11 illustrates the potency (IC$_{50}$) of compounds II and III against HER4 kinase
Figure 11:
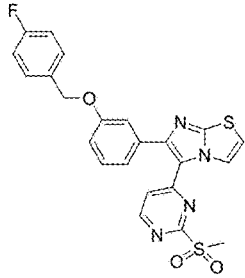
Figure 13:
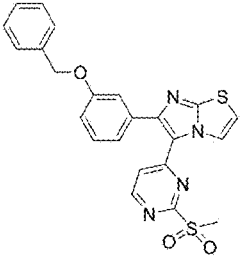
FIG. 13 illustrates the potency (IC$_{50}$) of compound III cytochrome P450 isozymes compared to ketoconazole (reference standard).

A study was conducted where novel derivatives of imidazothiazole- and imidazooxazole were evaluated for the first time as selective HER4 kinase inhibitors for their antiproliferative effects in cancer cells.

The novel derivatives featured an —OH group directly bonded to the phenyl ring and it was found that meta substituents have more proper orientation at the receptor site than para, and that hydrophobic substituents on the phenolic group, especially benzyl and 4-fluorobenzyl, are more active than hydrophilic ones.

The advantage of these novel derivatives derives from their ability to kill cancer cells with high selectivity and less toxicity and side effects. So far, no disadvantages have been found. Without being bound to any particular theory, it is believed that, should any disadvantages be found, they can be overcome by modification of their structure to attain better properties.

In one embodiment, disclosed herein are two novel imidazothiazole selective HER4 kinase inhibitors for the treatment of cancer.

In a first aspect of the present disclosure, there is provided a compound according to formula I:

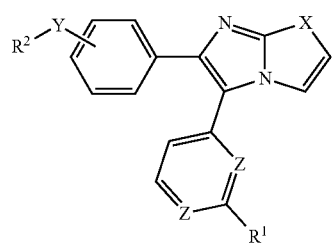

wherein:
X=S, O, NH, N—(C1-6 alkyl), N-(3-7 membered cycloalkyl);
Y=O, NH, S (para or meta or ortho);
Z=CH, N;
$R^1$=H, $SO_2CH_3$, $SO_2NH_2$, $SO_2NH(C_1-C_6)$alkyl, $NH_2$, Nalkyl, NH-aralkyl;
$R^2$=H, C1-6 alkyl or isoalkyl, C3-8 cycloalkyl, arylmethyl, arylethyl, arylpropyl, haloarylmethyl, haloarylethyl, heteroarylmethyl, heteroarylethyl, heteroarylpropyl, heteroarylalkenyl, heteroarylalkynyl, alkenyl, and alkynyl.

In one embodiment of the present disclosure, there is provided a compound according to formula (I.A):

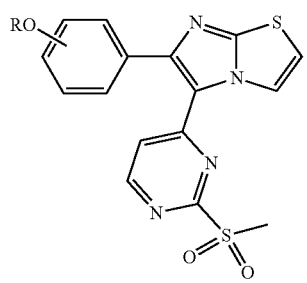

In a preferred embodiment of the present disclosure, there is provided a compound according to formula (II):

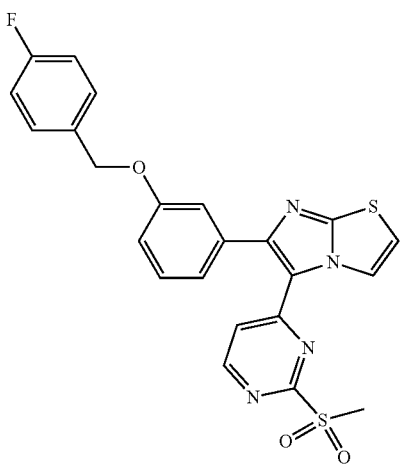 [SMILES: CS(=O)(=O)c1nccc(-c2c(-c3cccc(OCc4ccc(F)cc4)c3)nc3sccn23)n1]

In a most preferred embodiment of the present disclosure, there is provided a compound according to formula (III):

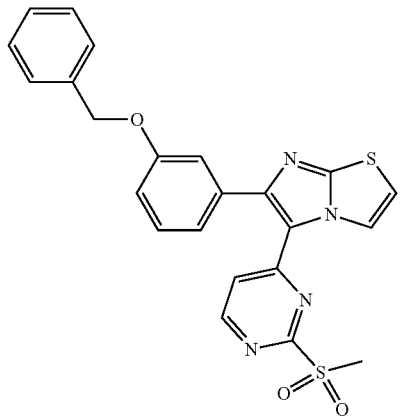 [SMILES: CS(=O)(=O)c1nccc(-c2c(-c3cccc(OCc4ccccc4)c3)nc3sccn23)n1]

In a second aspect of the present disclosure, there is provided a method of treating a subject afflicted by a cancer associated with an altered expression of HER4 kinases, by administering to the subject a therapeutically effective amount of compound I, or a pharmaceutically acceptable salt thereof, and one or more pharmaceutical excipients.

In one exemplary embodiment of the above-mentioned treatment, wherein the compound is a compound according to formula (I.A):

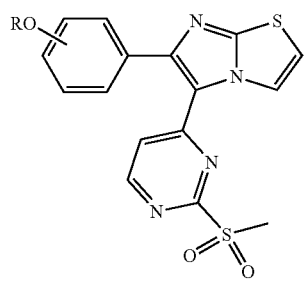

In a further embodiment of the above-mentioned treatment, the compound is a compound according to formula (II):

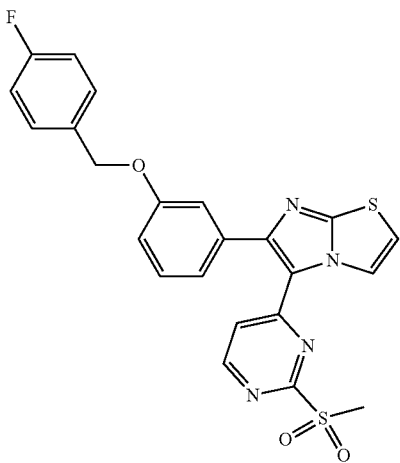 [SMILES: CS(=O)(=O)c1nccc(-c2c(-c3cccc(OCc4ccc(F)cc4)c3)nc3sccn23)n1]

In a preferred embodiment of the above-mentioned treatment, the compound is a compound according to formula (III):

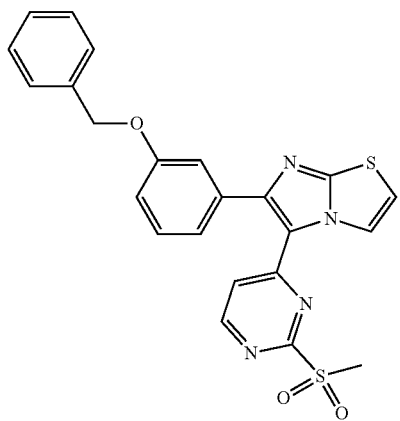 [SMILES: CS(=O)(=O)c1nccc(-c2c(-c3cccc(OCc4ccccc4)c3)nc3sccn23)n1]

Compounds described in the present disclosure show high selectivity and potency against HER4 kinase that is overexpressed in several types of cancer (e.g., breast cancer). No other imidazothiazole and imidazooxazole derivatives had been reported as HER4 inhibitors at the time of the invention. The results reported herein show these compounds can be useful in the treatment of cancer patients. Consequently, successful protocols can be translated for therapy of these patients.

Compositions featuring the aforementioned compounds may be specially formulated for administration in solid or liquid form, including those adapted for the following: (1) oral administration, for example, drenches (aqueous or nonaqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin. propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations may conveniently be presented in unit dosage form and may be prepared by any methods well known in the art of pharmacy. The amount of compound which can be combined with a carrier material to produce a single dosage form will vary depending upon the subject being treated, the particular mode of administration. The amount of an active ingredient which can be combined with a carrier material to produce a single dosage form will usually be that amount of the compound which produces a therapeutic effect. Usually, out of one hundred percent, this amount will range from about 1 wt % to about 99 wt % of active ingredient, preferably from about 5 wt % to about 70 wt %, most preferably from about 10 wt % to about 30 wt %.

In certain embodiments, a formulation of the compound includes an excipient selected from the group consisting of cyclodextrins, liposomes, micelle forming agents, e.g., bile acids, and polymeric carriers, e.g., polyesters and polyanhydrides; and an active ingredient that may be the compound and/or one of its pharmaceutically acceptable derivatives. In certain embodiments, an aforementioned formulation renders orally bioavailable a compound or its derivative.

Methods of preparing these formulations or compositions include the step of bringing into association the compound with the carrier and, optionally, one or more accessory ingredients. Usually, the formulations are prepared by uniformly and intimately bringing into association a compound of the present invention with liquid carriers, or finely divided solid carriers, or both, and then, if necessary, shaping the product.

Liquid dosage forms for oral administration of the compound include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A formulation of the compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also include buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

The tablets, and other solid dosage forms of the formulation of the compound, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of the compound for rectal or vaginal administration may be presented as a suppository, which may be prepared by the compound with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of the compound include powders, sprays, ointments, pastes, creams, lotions, gels, solutions, patches and inhalants. The extract may be mixed under sterile conditions with a pharmaceutically-acceptable carrier, and with any preservatives, buffers, or propellants which may be required. The ointments, pastes, creams and gels may contain, in addition to an extract, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an extract, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Powders and sprays can contain, in addition to an extract, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the compound to the body. Such dosage forms can be made by dissolving or dispersing an extract in the proper medium. Absorption enhancers can also be used to increase the flux of the extract or dispersing the extract in a polymer matrix or gel.

Pharmaceutical compositions suitable for parenteral administration include one or more components of the compound in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compound may be formulated into pharmaceutically-acceptable dosage forms by conventional methods known to those of skill in the art. The compound may be formulated for administration in any convenient way for use in human or veterinary medicine, by analogy with other pharmaceuticals.

In certain embodiments, the above-described pharmaceutical compositions include the compound, a chemotherapeutic agent, and optionally a pharmaceutically acceptable carrier. Alternatively, the terms "chemotherapeutic agent" or "therapeutic agent" include, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

Methods of Cancer Treatment

The above compound compositions may be used in novel therapeutic methods of treatment in cancer patients. The methods include administering to a subject an effective amount of a pharmaceutical compound composition. In representative embodiments, the subject suffers from a liver cancer. In specific embodiments, the type of liver cancer is a hepatocellular carcinoma (HCC), fibrolamellar HCC, cholangiocarcinoma, angiosarcoma, or liver cancer.

The above invention can be used to treat any cancer irrespective of the type or cause of the cancer, and irrespective of the genetic lesions associated with it, including, but not limited to cancer, pre-cancerous cells, tumors, neoplasms, and non-malignant tumors can also be treated. Cancers that can be treated include, e.g., cancers which are primary, which arise from a primary tumor at a secondary metastatic site; which have been treated by surgery (e.g., entirely removed, surgical resection, etc); which have been treated by chemotherapy, radiation, radiofrequency ablation, and/or any other adjunct to drug therapy; which have acquired drug-resistance; which are refractory to a chemotherapeutic agent.

The phrase "effective amount" indicates the amount of the compound which is effective to treat any symptom or aspect of the cancer. Effective amounts can be determined routinely. Further guidance on dosages and administration regimens is provided below.

The term "treatment" is used conventionally, e.g., the management or care of a subject for the purpose of combating, alleviating, reducing, relieving, improving, etc., one or more of the symptoms associated with a cancer, including all cancers mentioned herein and in Table 1. Administering effective amounts of the compound can treat one or more aspects of the cancer disease, including, but not limited to, causing tumor regression; causing cell death; causing apoptosis; causing necrosis; inhibiting cell proliferation; inhibiting tumor growth; inhibiting tumor metastasis; inhibiting tumor migration; inhibiting tumor invasion; reducing disease progression; stabilizing the disease, reducing or inhibiting angiogenesis; prolonging patient survival; enhancing patient's quality of life; reducing adverse symptoms associated with cancer; and reducing the frequency, severity, intensity, and/or duration of any of the aforementioned aspects.

The term "subject" in accordance with the present invention, includes, e.g., mammals, such as dogs, cats, horses, rats, mice, monkeys, and humans.

In other embodiments, types of cancer which can be treated in accordance with present invention include, but are not limited to: Cell Adult Acute Lymphoblastic Leukemia; Blastic Phase Chronic Myelogenous Leukemia; Bone Metastases; Brain Tumor; Breast Cancer; Cancer; Central Nervous System Cancer; Childhood Acute Lymphoblastic Leukemia; Childhood Acute Lymphoblastic Leukemia in Remission; Childhood Central Nervous System Germ Cell Tumor; Childhood Chronic Myelogenous Leukemia; Childhood Soft Tissue Sarcoma; Chordoma; Chronic Eosinophilic Leukemia (CEL); Chronic Idiopathic Myelofibrosis; Chronic Myelogenous Leukemia, Chronic Myeloid Leukemia; Chronic Myelomonocytic Leukemia; Chronic Phase Chronic Myelogenous Leukemia; Colon Cancer; Colorectal Cancer; Dermatofibrosarcoma; Dermatofibrosarcoma Protuberans (DFSP); Desmoid Tumor; Eosinophilia; Epidemic Kaposi's Sarcoma, Essential Thrombocythemia; Ewing's Family of Tumors; Extensive Stage Small Cell Lung Cancer; Fallopian Tube Cancer; Familiar Hypereosinophilia; Fibrosarcoma; Gastric Adenocarcinoma; Gastrointestinal Neoplasm; Gastrointestinal Stromal Tumor; Glioblastoma; Glioma; Gliosarcoma; Grade I Meningioma; Grade I Meningioma; Grade III Meningioma; Hematopoietic and Lymphoid Cancer, High-Grade Childhood Cerebral Astrocytoma; Hypereosinophilic Syndrome; Idiopathic Pulmonary Fibrosis, L1 Adult Acute Lymphoblastic Leukemia, L2 Adult Acute Lymphoblastic Leukemia; Leukemia, Lymphocytic, Acute L2; Leukemia, Myeloid, Chronic; Leukemia, Myeloid, Chronic Phase; Liver Dysfunction and Neoplasm; Lung Disease; Lymphoid Blastic Phase of Chronic Myeloid Leukemia; Male Breast Cancer, Malignant Fibrous Histiocytoma; Mastocytosis; Meningeal Hemangiopericytoma, Meningioma; Meningioma; Meningioma; Metastatic Cancer; Metastatic Solid Tumors; Myelofibrosis; Myeloid Leukemia, Chronic; Myeloid Leukemia, Chronic Accelerated-Phase; Myeloid Leukemia, Chronic, Chronic-Phase; Myeloid Metaplasia; Myeloproliferative Disorder (MPD) with Eosinophilia; Neuroblastoma; Non-T, Non-B Childhood Acute Lymphoblastic Leukemia, Oligodendroglioma;

Osteosarcoma; Ovarian Germ Cell Tumor; Ovarian Low Malignant Potential Tumor; Ovarian Neoplasms; Pancreatic Cancer; Pelvic Neoplasms; Peritoneal Cavity Cancer; Peritoneal Neoplasms; Philadelphia Chromosome Positive Chronic Myelogenous Leukemia; Philadelphia Positive Acute Lymphoblastic Leukemia; Philadelphia Positive Chronic Myeloid Leukemia in Myeloid Blast Crisis; Polycythemia Vera, Pulmonary Fibrosis; Recurrent Adult Brain Tumor; Recurrent Adult Soft Tissue Sarcoma; Recurrent Breast Cancer; Recurrent Colon Cancer; Recurrent Esophageal Cancer; Recurrent Gastric Cancer; Recurrent Glioblastoma Multiforme (GBM); Recurrent Kaposi's Sarcoma; Recurrent Melanoma, Recurrent Merkel Cell Carcinoma, Recurrent Ovarian Epithelial Cancer; Recurrent Pancreatic Cancer; Recurrent Prostate Cancer; Recurrent Rectal Cancer; Recurrent Salivary Gland Cancer; Recurrent Small Cell Lung Cancer; Recurrent Tumors of the Ewing's Family; Recurrent Uterine Sarcoma; Relapsing Chronic Myelogenous Leukemia; Rheumatoid Arthritis; Salivary Gland Adenoid Cystic Carcinoma; Sarcoma; Small Cell Lung Cancer; Stage U Melanoma, Stage Ii Merkel Cell Carcinoma; Stage III Adult Soft Tissue Sarcoma; Stage III Esophageal Cancer; Stage 111 Merkel Cell Carcinoma; Stage ill Ovarian Epithelial Cancer; Stage III Pancreatic Cancer; Stage III Salivary Gland Cancer; Stage IUB Breast Cancer; Stage UIC Breast Cancer, Stage IV Adult Soft Tissue Sarcoma; Stage IV Breast Cancer; Stage IV Colon Cancer; Stage IV Esophageal Cancer; Stage IV Gastric Cancer, Stage IV Melanoma; Stage IV Ovarian Epithelial Cancer; Stage IV Prostate Cancer; Stage IV Rectal Cancer; Stage IV Salivary Gland Cancer; Stage IVA Pancreatic Cancer; Stage IVB Pancreatic Cancer; Systemic Mastocytosis, T-CeII Childhood Acute Lymphoblastic Leukemia; Testicular Cancer; Thyroid Cancer; Unresectable or Metastatic Malignant Gastrointestinal Stromal Tumor (GIST); Unspecified Adult Solid Tumor; Untreated Childhood Brain Stem Glioma; Uterine Carcinosarcoma, and Uterine Sarcoma. Diseases which can be treated in accordance with present invention include, e.g., diseases which are treated with gefitinib, such as, but not limited to: Adenocarcinoma of the Colon; Adenocarcinoma of the Esophagus; Adenocarcinoma of the Lung; Adenocarcinoma of the Prostate; Adenocarcinoma of the Rectum; Advanced Adult Primary Liver Cancer; Advanced Non-Nasopharyngeal Head and Neck Carcinoma; Anaplastic Astrocytoma; Anaplastic Oligodendroglioma; Anaplastic Thyroid Cancer; Bladder Cancer; Brain Tumor; Breast Cancer; Breast Cancer in Situ, Breast Neoplasms, Bronchoalveolar Cell Lung Cancer; Cancer of the Fallopian Tube; Carcinoma, Squamous Cell; Cervix Neoplasms; Colon Cancer; Colorectal Cancer; Epithelial Mesothelioma; Esophageal Cancer; Esophagogastric Cancer; Follicular Thyroid Cancer; Gastric Cancer; Gastrinoma; Gastrointestinal Carcinoid; Giant Cell Glioblastoma; Glioblastoma; Glioblastoma Multiforme; Head and Neck Cancer; Hepatocellular Carcinoma; Hypopharyngeal Cancer; Inoperable Locally Advanced Squamous Cell Carcinoma of Head and Neck; Insulinoma; Intraductal Breast Carcinoma; Islet Cell Carcinoma; Large Cell Lung Cancer; Laryngeal Cancer; Lip and Oral Cavity Cancer; Lip Cancer; Liver Cancer, Lung Adenocarcinoma With Bronchiole-Alveolar Feature; Lung Cancer; Male Breast Cancer; Medullary Thyroid Cancer; Meningeal Tumors; Metastatic Colorectal Cancer; Metastatic Gastrointestinal Carcinoid Tumor; Metastatic Pancreatic Carcinoma; Mixed Gliomas; Myelogenous Leukemia, Acute; Nasopharyngeal Carcinoma; Neuroblastoma; Non-Metastatic (T2-T4, N0-N3, MO, Stages II and III) and Histologically-Confirmed Intestinal GC; Non-Metastatic Prostate Cancer; Nonresectable Adrenocortical Carcinoma; Non-Small Cell Lung Cancer; Nose Cancer; Oligodendroglial Tumors; Oral Cancer; Oropharyngeal Cancer; Osteosarcoma; Ovarian Cancer; Ovarian Neoplasms; Pancreatic Cancer; Papillary Thyroid Cancer; Peritoneal Carcinoma, Pharynx Cancer, Pneumonic-Type Adenocarcinoma (P-ADC); Primary Hepatocellular Carcinoma; Prostate Cancer; Rectal Cancer; Recurrent Adult Primary Liver Cancer; Recurrent Breast Cancer; Recurrent Colon Cancer; Recurrent Endometrial Cancer, Recurrent Esophageal Cancer; Recurrent Glioblastoma; Recurrent Rectal Cancer; Recurrent Skin Cancer; Refractory Germ Cell Tumors Expressing EGRF; Renal Cell Cancer; Rhabdomyosarcomas; Sarcomatous Mesothelioma, Skin Cancer; Soft Tissue Sarcoma; Squamous Cell Carcinoma of the Esophagus, Squamous Cell Carcinoma of the Head and Neck; Squamous Cell Carcinoma of the Skin; Squamous Cell Lung Cancer; Stage II Esophageal Cancer; Stage III Esophageal Cancer, Synovial Sarcoma; Thorax and Respiratory Cancer; Throat Cancer; Thyroid Cancer; Transitional Cell Cancer of the Renal Pelvis and Ureter; Transitional Cell Carcinoma of the Bladder; Tubal Carcinoma; Unspecified Childhood Solid Tumor, Untreated Childhood Brain Stem Glioma; Urethral Cancer.

As anticipated above, the compound may be administered by any appropriate route, for example orally, parenterally, topically, or rectally. It will be appreciated that the preferred route may vary with, for example, the condition of the recipient of the compound and the cancer to be treated. In certain embodiments, the extract may be especially suitable for the preparation of pharmaceuticals for intravenous administration, such as intravenous injection or infusion, provided that it does not contain components with serum-precipitating and/or haemagglutinating properties which disturb such an application. The extract may therefore be provided in the form of ampoule preparations which are directed to intravenous administration. In still other embodiments, the method comprises systemic administration of a subject composition to a subject.

Also provided are methods of treating cancer, for example liver cancer, which include administering the compound in conjunction with a chemotherapeutic agent to a subject. Conjunctive therapy includes sequential, simultaneous and separate, or co-administration of the compound and the chemotherapeutic agent in a way that the therapeutic effect of the chemotherapeutic agent is not entirely disappeared when the compound is administered. In certain embodiments, compound and the chemotherapeutic agent may be compounded together in the same unitary pharmaceutical composition including both entities. Alternatively, the combination of compound and chemotherapeutic agent may be administered separately in separate pharmaceutical compositions, each including one of the compound and chemotherapeutic agent in a sequential manner wherein, for example, the compound or the chemotherapeutic agent is administered first and the other second.

Exemplary doses of the compound in the range from about 0.001, 0.01, 0.1, 0.5, 1, 10, 15, 20, 25, 50, 100, 200, 300, 400, 500, 600, or 750 to about 1000 mg/day per kg body weight of the subject. In certain embodiments, the dose of the compound will typically be in the range of about 100 mg/day to about 1000 mg/day per kg body weight of the subject, specifically in the range of about 200 mg/day to about 750 mg/day per kg, and more specifically in the range of about 250 mg/day to about 500 mg/day per kg. In an embodiment, the dose is in the range of about 50 mg/day to about 250 mg/day per kg. In a further embodiment, the dose in the range of about 100 mg/day to about 200 mg/day per kg. In an embodiment, the dose is in the range of about 15 mg/day to 60 mg/day per kg. In a further embodiment, the dose is in the range of about 20 mg/day to 50 mg/day per kg. In an additional embodiment, the dose is in the range of about 25 mg/day to 45 mg/day per kg.

The combined use of the compound and other chemotherapeutic agents may reduce the required dosage for any individual component because the onset and duration of effect of the different components may be complementary. In such combination therapies, the different active agents may be delivered together or separately, and simultaneously or at different times within the day.

The data obtained from cell culture assays and animal studies may be used in formulating a range of dosage for use in humans. For example, effective dosages achieved in one animal species may be extrapolated for use in another animal, including humans, as illustrated in the conversion table of FIG. 15 where human equivalent dose (HED) dosage factors based on body surface area of other species are reported. [1]. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For the compound or combinations of the compound and other chemotherapeutic agents, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

In a third aspect of the present disclosure, there is provided a kit for treating a subject afflicted by a cancer associated with an altered expression of one or more kinases, the kit comprising the compound I or a pharmaceutically acceptable salt thereof, and one or more pharmaceutical excipients.

The present invention provides kits for novel therapeutic methods in cancer patients. For example, a kit may include one or more pharmaceutical compositions of the compound as described above. The compositions may be pharmaceutical compositions comprising a pharmaceutically acceptable excipient. In other embodiments involving kits, this invention provides a kit including the compound, optionally a chemotherapeutic agent, and optionally instructions for their use in the treatment of cancer. In still other embodiments, the invention provides a kit comprising one more pharmaceutical compositions and one or more devices for accomplishing administration of such compositions. For example, a subject kit may comprise a pharmaceutical composition and catheter for accomplishing direct intraarterial injection of the composition into a cancer. In an embodiment, the device is an intraarterial catheter. Such kits may have a variety of uses, including, for example, therapy, diagnosis, and other applications.

Definitions

As used in this description and the accompanying claims, the following terms shall have the meanings indicated, unless the context otherwise requires:

As used herein, "treatment" is understood to refer to the administration of a drug or drugs to a patient suffering from cancer.

As used herein, the term "therapeutically effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Synthesis of Intermediate Compounds 1c,d

To a solution of compound 1a,b (0.2 mmol) in anhydrous dichloromethane (1 mL), $BBr_3$ (0.16 mL of a 1M solution in methylene chloride, 2.4 mmol) was added dropwise at −78° C. under inert atmosphere. The mixture was swirled at −78° C. for 30 min, then overnight at room temperature. The mixture was quenched with aqueous potassium carbonate until alkalinization of the reaction. Ethyl acetate (30 mL) was added, the mixture was stirred, and the organic layer was separated. The aqueous layer was extracted again with ethyl acetate (3×20 mL). The organic extract was washed with saline solution, and then dried over anhydrous $Na_2SO_4$. The crude product was collected after evaporation of the solvent, then purified by flash column chromatography (silica gel, hexane-ethyl acetate) to yield the target hydroxyl products 1c,d.

Synthesis of Compounds of Formula II and III

To a solution of compound 1c (100 mg, 0.27 mmol) in anhydrous DMF (2 mL), sodium hydride (60% dispersion in mineral oil, 0.41 mmol, 16.2 mg) was added. After stirring at room temperature for 5 min, benzyl chloride or 4-fluorobenzyl chloride (0.54 mmol) was added thereto. The reaction mixture was allowed to stir at room temperature for 1 h, then quenched with water (5 mL) and ethyl acetate (5 mL). After separation of the organic layer, the aqueous layer was extracted again with ethyl acetate (3×5 mL). The organic extract was washed with saline solution, and then dried over anhydrous $Na_2SO_4$. The crude product was collected after evaporation of the solvent, then purified by flash column chromatography (silica gel, hexane-ethyl acetate) to yield the purified target product.

Spectral Data of Compound III (6-(3-(Benzyloxy) phenyl)-5-(2 (methylsulfonyl)pyrimidin-4-yl)imidazo[2,1-b]thiazole)

$^1$H NMR ($CDCl_3$, 500 MHz) δ 8.87 (d, 1H, J=4.5 Hz), 8.42 (d, 1H, J=5.5 Hz), 7.43-7.31 (m, 7H), 7.24-7.19 (m, 2H), 7.12 (d, 1H, J=8.0 Hz), 7.60 (d, 1H, J=4.5 Hz), 5.11 (s, 2H), 3.36 (s, 3H); $^{13}$C NMR ($CDCl_3$, 125 MHz) δ 165.8, 159.4, 157.5, 156.9, 154.5, 153.3, 136.8, 135.6, 130.5, 128.8, 128.2, 127.6, 123.4, 121.7, 119.7, 117.8, 116.8, 115.2, 114.0, 70.2, 39.4; LC/MS m/z: 463.0 ($M^+$+1); CHN analysis: calculated C: 59.72%, H: 3.92%, N: 12.11%; found: C: 59.66%, H: 3.88%, N: 12.19%.

Spectral Data of Compound II (6-(3-(4-Fluorobenzyloxy)phenyl)-5-(2-(methylsulfonyl)pyrimidin-4-yl)imidazo[2,1-b]thiazole)

$^1$H NMR (CD$_3$OD, 300 MHz) S 8.46 (d, 1H, J=6.0 Hz), 8.07 (d, 1H, J=7.2 Hz), 7.35-7.25 (m, 4H), 7.08-6.93 (m, 6H), 4.97 (s, 2H), 3.20 (s, 3H); $^{13}$C NMR (CD$_3$OD, 75 MHz) S 160.5, 159.6, 159.2, 155.1, 136.5, 134.4, 131.4, 130.7, 130.6, 123.5, 122.9, 117.5, 116.6, 116.4, 116.1, 116.0, 115.7, 70.4, 39.6; LC/MS m/z: 480.8 (M$^+$+1); CHN analysis: calculated C: 57.49%, H: 3.57%, N: 11.66%; found: C: 57.42%, H: 3.68%, N: 11.56%.

EXPERIMENTAL EXAMPLES

Antiproliferative Activity

In this study, sixty cancer cell lines of nine different cancer types were used for screening the antiproliferative activity of the target molecules. Compounds (I.A) exhibited the highest activity. The cell lines were obtained from the National Cancer Institute (NCI, Bethesda, Maryland, USA).

Cell Viability Assay

MTT assay was performed to assess the effect of the synthesized compounds on cell viability and to determine the half-maximal inhibitory concentration (IC$_{50}$) of the most active compounds as mentioned before with some minor modifications. The cells were seeded in 96-well tissue culture plates with a density of 4×10$^4$/well and incubated overnight. After that, cells were treated with the newly synthesized compounds or Sorafenib as a positive control for 48 h. DMSO (vehicle) was used as a negative control. After treatment, the media was removed, and cells were incubated for 2 h at 37° C. with 200 μL media containing 0.5 mg/mL of MTT tetrazolium dye (Sigma-Aldrich). Finally, the media were removed and 200 μL of DMSO was added to solubilize the formed violet crystals. Absorbance was measured at 570 nm using a microplate reader (Thermo Scientific, Massachusetts, USA).

Kinase Profiling

In a final reaction volume of 25 μL, kinase (5-10 mU) is incubated with 25 mM Tris pH 7.5, 0.02 mM EGTA, 0.66 mg/mL myelin basic protein, 10 mM magnesium acetate and [γ$^{33}$P-ATP] (specific activity approx. 500 cpm/pmol, concentration as required). The reaction is initiated by the addition of the Mg-ATP mix. After incubation for 40 min at room temperature, the reaction is stopped by the addition of 5 μL of a 3% phosphoric acid solution. 10 μL of the reaction is then spotted onto a P30 filtermat and washed three times for 5 min in 75 mM phosphoric acid

REFERENCES

[1] Nair, A. B., Jacob S. (2016). A simple practical guide for dose conversion between animal and human. J Basic Clin Pharma 2016, 7:27-31.

What is claimed is:

1. The compound according to formula II, or pharmaceutically acceptable salt thereof:

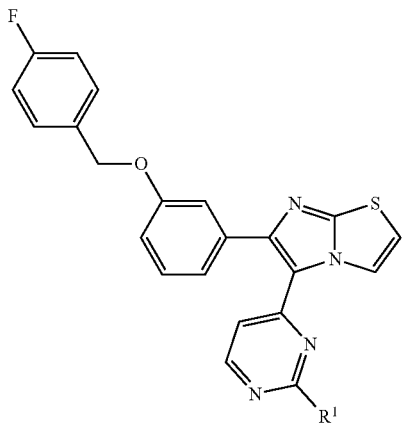

(II)

wherein:
R$^1$ is selected from the group consisting of: —SO$_2$CH$_3$, —SO$_2$NH$_2$ and —SO$_2$NHalkyl(C$_1$-C$_6$).

2. A pharmaceutical composition, comprising a therapeutically effective amount of the compound, or pharmaceutically acceptable salts thereof, of claim 1, and one or more pharmaceutical excipients.

3. The compound according to formula III, or pharmaceutically acceptable salt thereof:

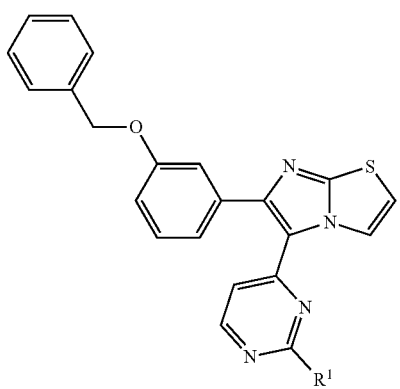

(III)

wherein R$^1$ is selected from the group consisting of: —SO$_2$CH$_3$, —SO$_2$NH$_2$, and —SO$_2$NHalkyl(C$_1$-C$_6$).

4. The compound according to claim 1, wherein O is a meta substituent.

5. The compound according to claim 1, wherein O is an ortho substituent.

6. The compound according to claim 1, wherein O is a para substituent.

7. A pharmaceutical composition, comprising a therapeutically effective amount of the compound, or pharmaceutically acceptable salts thereof, of claim 4, and one or more pharmaceutical excipients.

8. A pharmaceutical composition, comprising a therapeutically effective amount of the compound, or pharmaceutically acceptable salts thereof, of claim 5, and one or more pharmaceutical excipients.

9. A pharmaceutical composition, comprising a therapeutically effective amount of the compound, or pharmaceutically acceptable salts thereof, of claim 3, and one or more pharmaceutical excipients.

* * * * *